United States Patent [19]

Jacob et al.

[11] Patent Number: 5,985,312
[45] Date of Patent: Nov. 16, 1999

[54] METHODS AND COMPOSITIONS FOR ENHANCING THE BIOADHESIVE PROPERTIES OF POLYMERS

[75] Inventors: Jules S. Jacob, Taunton; Edith Mathiowitz, Brookline, both of Mass.

[73] Assignee: Brown University Research Foundation, Providence, R.I.

[21] Appl. No.: 08/592,565

[22] Filed: Jan. 26, 1996

[51] Int. Cl.⁶ .................... A61K 9/14; A61K 15/54; A61K 51/00; A61K 47/02
[52] U.S. Cl. .................... 424/434; 424/489; 424/9.3
[58] Field of Search .................... 424/9.1, 9.3, 111, 424/434

[56] References Cited

U.S. PATENT DOCUMENTS

| | | | |
|---|---|---|---|
| 2,675,619 | 6/1954 | Cone | 33/76 |
| 2,677,700 | 5/1954 | Jackson et al. | 260/488 |
| 2,979,578 | 4/1961 | Curtis et al. | 200/32 |
| 3,036,118 | 5/1962 | Jackson et al. | 260/484 |
| 3,535,307 | 10/1970 | Moss et al. | 260/209 |
| 3,829,506 | 8/1974 | Schmolka et al. | 260/615 |
| 4,861,627 | 8/1989 | Mathiowitz et al. | 427/213.31 |
| 4,938,763 | 7/1990 | Dunn et al. | 604/891.1 |
| 4,976,968 | 12/1990 | Steiner | 424/491 |
| 5,019,400 | 5/1991 | Gombotz et al. | 424/497 |
| 5,213,788 | 5/1993 | Ranney | 424/9 |
| 5,219,554 | 6/1993 | Groman et al. | 424/9 |

(List continued on next page.)

FOREIGN PATENT DOCUMENTS

| | | |
|---|---|---|
| 0 200 508 A2 | 12/1986 | European Pat. Off. . |
| 0 333 523 A2 | 3/1989 | European Pat. Off. . |
| 0 363 224 A1 | 4/1990 | European Pat. Off. . |
| 0 526 862 A1 | 2/1993 | European Pat. Off. . |
| 0 625 353 A1 | 11/1994 | European Pat. Off. . |
| 44 34 929 A1 | 1/1996 | Germany . |
| WO 91/06286 | 5/1991 | WIPO . |
| WO 91/06287 | 5/1991 | WIPO . |
| WO 91/14733 | 10/1991 | WIPO . |
| WO 93/21906 | 11/1993 | WIPO . |
| WO 95/33434 | 12/1995 | WIPO . |

OTHER PUBLICATIONS

Lee, K. et al., "Design of Oral Patches for the Treatment of Aphthous Stomatitis: Drug Layer", Yakche Hakhoechi 25(4):339–45 (S. Korea 1995); Chemical Abstracts 124(22), Abstract No. 298738 (May 27, 1996).

Allen, et al., "Mucus Glycoprotein Structure, Gel Formation and Gastrointestinal Mucus Function" in J. Nugent & M. O'Connor, Eds., Mucus and Mucosa, *Ciba Foundation Symposium 109*, Pitman, London, 137:137–156 (1984).

(List continued on next page.)

*Primary Examiner*—Peter F. Kulkosky
*Attorney, Agent, or Firm*—Arnall Golden & Gregory LLP

[57] ABSTRACT

Methods and compositions are provided for enhancing the bioadhesive properties of polymers used in drug delivery devices. The bioadhesive properties of a polymer are enhanced by incorporating a metal compound into the polymer to enhance the ability of the polymer to adhere to a tissue surface such as a mucosal membrane. Metal compounds which enhance the bioadhesive properties of a polymer include water-insoluble metal compounds such as water-insoluble metal oxides, including oxides of calcium, iron, copper and zinc. The metal compounds can be incorporated within a wide range of polymers including proteins, polysaccharides and synthetic biocompatible polymers. In one embodiment, metal oxides can be incorporated within polymers used to form or coat drug delivery devices, such as microspheres, which contain a drug or diagnostic agent. The metal oxides can be provided in the form of a fine dispersion of particles on the surface of a polymer that coats or forms the devices, which enhances the ability of the devices to bind to mucosal membranes. The polymers, for example in the form of microspheres, have improved ability to adhere to mucosal membranes, and thus can be used to deliver a drug or diagnostic agent via any of a range of mucosal membrane surfaces including those of the gastrointestinal, respiratory, excretory and reproductive tracts.

15 Claims, 1 Drawing Sheet

U.S. PATENT DOCUMENTS

| | | | |
|---|---|---|---|
| 5,271,961 | 12/1993 | Mathiowitz et al. | 427/213.31 |
| 5,427,767 | 6/1995 | Kresse et al. | 424/9.32 |
| 5,498,421 | 3/1996 | Grinstaff et al. | 424/9.3 |
| 5,527,321 | 6/1996 | Unger | 424/9.3 |
| 5,547,682 | 8/1996 | Chagnon et al. | 424/497 |

OTHER PUBLICATIONS

L.R. Beck, et al., "A New Long–Acting Injectable Microcapsule System For The Administration Of Progesterone," *Fertil. Steril.*, 31:545–551 (1979).

S. Benita, et al., "Characterization of Drug–Load poly(d–l–lactide) Microsphere," *J. Pharm. Sci.*, 73:1721–1724 (1984).

Duchene, et al., "Pharmaceutical And Medical Aspects of Bioadhesive Systems For Drug Administration," *Drug Dev. Ind. Pharm.*, 14:283–318 (1988).

E. Edelman, et al., "Perivascular and Intravenous Administration of Basic Fibroblast Growth Factor: Vascular and Solid Organ Deposition," *Proc. Natl. Acad. Sci., USA* 30:1513–1517 (1993).

Furia, Ed., *CRC Handbook of Food Additives*, Cleveland, OH, 1968.

Gurney, et al., "Bioadhesive Intraoral Release Systems: Design, Testing and Analysis," *Biomaterials*, 5:336–340 (1984).

K. Harada, et al., "Basic Fibroblast Growth Factor Improves Myocardial Function in Chronically Ischemic Porcine Hearts," *J. Clin. Invest.*, 94:623–630 (1994).

Horowitz, M.I. and Pigman, W., "Use of Enzymes in Elucidation of Structure," *The Glycoconiugates*, pp. 560 (New York:Academic Press, Inc. 1977).

Horowitz, M.I., "Mucopolysaccharides and Glycoproteins of the Alimentary Tract" in Alimentary Canal (eds. C.F. Code), pp.1063–1085 (Washington: American Physiological Society, 1967).

Labat–Robert, J. and Decaeus, "Glycoprotéines Du Mucus Gastrique: Structure Fonctions Et Pathologie et Biologie", *Path. Biol.*, 24:241 (1979).

Lehr, et al., "Intestinal Transit of Bioadhesive Microspheres in an in Situ Loop In The Rat –A Comparative Study With Copolymers And Blends Based On Poly(Acrylic Acid)," *J. Controlled Rel. Soc.*, 13:51–62 (1990).

Labhasetwar, V., et al., "Sotalol Controlled–Release Systems for Arrhythmias: In Vitro Characterization, in Vivi Drug Disposition and Electrophysilolgic Effects," *J. Pharmaceutical Sci.*, 83(2):156–164 (1994).

E. Mathiowitz, et al., "Morphology of Polyanhydride Microsphere Delivery Systems," *J. Scanning Microscopy*, 4:329–340 (1990).

Mathiowitz et al., "Novel Microcapsules For Delivery Systems," *Reactive Polymers*, 6:275–283 (1987).

Mikos et al., "Interaction of Polymer Microspheres with Mucin Gels As A Means of Charaterizing Polymer Retention On Mucus," *J. Colloid Interface Sci.*, 143:366–373 (1991).

Park, et al., "Alternative Approaches to Oral Controlled Drug Delivery: Bioadhesives And In–Situ Systems," in J.M. Anderson and S.W. Kim, Eds., *Recent Advances in Drug Delivery*, Plenum Press, New York, 1984, pp. 163–183.

Pigman, W. & Gottschalk A., "Submaxillary Gland Glycoproteins" in Glycoproteins: Their Composition, Structure and Function (eds. A. Gottschalk), pp. 434–445 (Amsterdam: Elsevier Publishing Company, Inc., 1966).

Scawen, M. & Allen, A., "The Action of Proteolytic Enzymes on the Glycoprotein From Pig Gastric Mucus," *Biochemical Journal*, 163:363–368 (1977).

Smart, et al., "An In–vitro Investigation of Mucosa–adhesive Materials For Use In Controlled Drug Delivery," *J. Pharm. Pharmacol.*, 36:295–299 (1984).

Spiro, R.G., "Glycoproteins," *Annual Review of Biochemistry*, 39:599–638 (1970).

Tutwiler, et al., "A Pharmacologic Profile of McN–3495 [N–(1–methyl–2–pyrrolidinylidene)–N'–phenyl–l–pyrrolidnecarboximidamide], A New, Orally Effective Hypoglycemic Agent," *Diabetes*, 27:856–867 (1978).

METHODS AND COMPOSITIONS FOR ENHANCING THE BIOADHESIVE PROPERTIES OF POLYMERS

This invention was made with government support under Grant Number R01-GM-47636-0183 awarded by the National Institutes of Health. The government has certain rights in this invention.

BACKGROUND OF THE INVENTION

The present invention is generally in the area of polymeric drug delivery devices.

Controlled release systems for drug delivery are often designed to administer drugs in specific areas of the body. In the case of drug delivery via the gastrointestinal tract, it is critical that the drug not be entrained beyond the desired site of action and eliminated before it has had a chance to exert a topical effect or to pass into the bloodstream. If a drug delivery system can be made to adhere to the lining of the appropriate viscus, its contents will be delivered to the targeted tissue as a function of proximity and duration of the contact.

An orally ingested product can adhere to either the epithelial surface or the mucus. For the delivery of bioactive substances, it can be advantageous to have a polymeric drug delivery device adhere to the epithelium or to the mucous layer. Bioadhesion in the gastrointestinal tract proceeds in two stages: (1) viscoelastic deformation at the point of contact of the synthetic material into the mucus substrate, and (2) formation of bonds between the adhesive synthetic material and the mucus or the epithelial cells. In general, adhesion of polymers to tissues may be achieved by (i) physical or mechanical bonds, (ii) primary or covalent chemical bonds, and/or (iii) secondary chemical bonds (i.e., ionic). Physical or mechanical bonds can result from deposition and inclusion of the adhesive material in the crevices of the mucus or the folds of the mucosa. Secondary chemical bonds, contributing to bioadhesive properties, consist of dispersive interactions (i.e., Van der Waals interactions) and stronger specific interactions, which include hydrogen bonds. The hydrophilic functional groups primarily responsible for forming hydrogen bonds are the hydroxyl and the carboxylic groups.

Several microsphere formulations have been proposed as a means for oral drug delivery. These formulations generally serve to protect the encapsulated compound and to deliver the compound into the blood stream. Enteric coated formulations have been widely used for many years to protect drugs administered orally, as well as to delay release. Other formulations designed to deliver compounds into the blood stream, as well as to protect the encapsulated drug, are formed of a hydrophobic protein, such as zein, as described in PCT/U.S. Pat. No. 90/06430 and PCT/U.S. Pat. No. 90/06433; "proteinoids", as described in U.S. Pat. No. 4,976,968 to Steiner; or synthetic polymers, as described in European Patent application 0 333 523 by The UAB Research Foundation and Southern Research Institute. EPA 0 333 523 describes microparticles of less than ten microns in diameter that contain antigens, for use in oral administration of vaccines. The microparticles are formed of polymers such as poly(lactide-co-glycolide), poly(glycolide), polyorthoesters, poly(esteramides), polyhydroxybutyric acid and polyanhydrides, and are absorbed through the Peyer's Patches in the intestine, principally as a function of size.

Duchene et al., *Drug Dev. Ind. Pharm.*, 14, 283–318 (1988) is a review of the pharmaceutical and medical aspects of bioadhesive systems for drug delivery. Polycarbophils and acrylic acid polymers were noted as having the best adhesive properties. "Bioadhesion" is defined as the ability of a material to adhere to a biological tissue for an extended period of time. Bioadhesion is clearly one solution to the problem of inadequate residence time resulting from the stomach emptying and intestinal peristalsis, and from displacement by ciliary movement. For sufficient bioadhesion to occur, an intimate contact must exist between the bioadhesive and the receptor tissue, the bioadhesive must penetrate into the crevice of the tissue surface and/or mucus, and mechanical, electrostatic, or chemical bonds must form. Bioadhesive properties of polymers are affected by both the nature of the polymer and by the nature of the surrounding media.

Others have explored the use of bioadhesive polymers. PCT WO 93/21906, the disclosure of which is incorporated herein by reference, discloses methods for fabricating bioadhesive microspheres and for measuring bioadhesive forces between microspheres and selected segments of the gastrointestinal tract in vitro. Smart et al., *J. Pharm. Pharmacol.*, 36:295–299 (1984), reported a method to test adhesion to mucosa using a polymer coated glass plate contacting a dish of mucosa. A variety of polymeric materials were tested, including sodium alginate, sodium carboxymethyl-cellulose, gelatin, pectin and polyvinylpyrrolidone. Gurney et al., *Biomaterials*, 5:336–340 (1984) reported that adhesion may be effected by physical or mechanical bonds; secondary chemical bonds; and/or primary, ionic or covalent bonds. Park et al., "Alternative Approaches to Oral Controlled Drug Delivery: Bioadhesives and In-Situ Systems," in J. M. Anderson and S. W. Kim, Eds., "Recent Advances in Drug Delivery," Plenum Press, New York, 1984, pp. 163–183, reported a study of the use of fluorescent probes in cells to determine adhesiveness of polymers to mucin/epithelial surface, which indicated that anionic polymers with high charge density appear to be preferred as adhesive polymers.

Mikos et al., in *J. Colloid Interface Sci.*, 143:366–373 (1991) and Lehr et al., *J. Controlled Rel. Soc.*, 13:51–62 (1990) reported a study of the bioadhesive properties of polyanhydrides and polyacrylic acid, respectively, in drug delivery. Lehr et al. screened microparticles formed of copolymers of acrylic acid using an in vitro system and determined that the copolymer "Polycarbophil" has increased adhesion.

In general, gastrointestinal (GI) mucus is made of 95% water and 5% electrolytes, lipids, proteins and glycoproteins, as described by Spiro, R. G., *Annual Review of Biochemistry*, 39:599–638 (1970); and Labat-Robert, J. and Decaeus, C., *Pathologie et Biologie* (Paris), 24:241 (1979). However, the composition of the latter fraction can vary greatly. Proteins, including the protein core of the glycoproteins, can made up anywhere from 60 to 80% of this fraction. Horowitz, M. I., "Mucopolysaccharides and Glycoproteins of the Alimentary Tract" in *Alimentary Canal* (Eds. C. F. Code), pp. 1063–1085 (Washington: American Physiological Society, 1967). The glycoproteins typically have a molecular weight of approximately two million and consist of a protein core (approximately 18.6–25.6% by weight) with covalently attached carbohydrate side chains (approximately 81.4–74.4% by weight) terminating in either L-fucose or sialic acid residues. Spiro, R. G., *Annual Review of Biochemistry*, 39:599–638 (1970); Scawen, M. & Allen, A., "The Action of Proteolytic Enzymes on the Glycoprotein from Pig Gastric Mucus," *Biochemical Journal*, 163:363–368 (1977); Horowitz, M. I. and Pigman, W., *The*

*Glycoconjugates*, pp. 560 (New York: Academic Press, Inc., 1977); and Pigman, W. & Gottschalk, A., "Submaxillary Gland Glycoproteins" in *Glycoproteins: Their Composition, Structure and Function* (eds. A. Gottschalk), pp. 434–445 (Amsterdam: Elsevier Publishing Company, Inc., 1966). Species and location differences in the composition of these glycoproteins have been reported by Horowitz, M. I., "Mucopolysaccharides and Glycoproteins of the Alimentary Tract" in *Alimentary Canal* (eds. C. F. Code), pp. 1063–1085 (Washington: American Physiological Society, 1967).

It has been shown that the gastric mucous layer thickness typically varies from 5 to 200 μ in the rat and 10 to 400 μ in man. Occasionally, however, it can reach thicknesses as great as 1000 μ in man, as described by Spiro, R. G., "Glycoproteins," *Annual Review of Biochemistry*, 39:599–638 (1970); Labat-Robert, J. and Decaeus, C., *Pathologie et Biologie* (Paris) 24:241 (1979); and Allen et al., "Mucus Glycoprotein Structure, Gel Formation and Gastrointestinal Mucus Function" in J. Nugent & M. O'Connor, Eds., *Mucus and Mucosa, Ciba Foundation Symposium* 109, Pitman, London, 1984, pp. 137.

There is a need for methods for controlling or increasing the absorption of pharmaceutical agents from polymeric drug delivery devices such as polymeric microspheres through mucosal membranes. There also is a need for methods for delaying transit of the devices through nasal or gastrointestinal passages. It is therefore an object of the present invention to provide methods for improving the bioadhesive properties of polymeric drug delivery devices such as microspheres, tablets, capsules and stents. It is another object of the invention to provide methods for improving the adhesion of drug delivery devices such as microspheres to mucosal membranes including buccal and nasal membranes and membranes of the gastrointestinal and reproductive tracts. It is a further object of the invention to provide polymeric drug delivery devices with improved ability to bind to mucosal membranes which can be used to deliver a wide range of drugs or diagnostic agents in a wide variety of therapeutic applications.

SUMMARY OF THE INVENTION

Methods and compositions are provided for enhancing the bioadhesive properties of polymers used in drug delivery devices. The bioadhesive properties of a polymer are enhanced by incorporating a metal compound into the polymer to enhance the ability of the polymer to adhere to a tissue surface such as a mucosal membrane. Metal compounds which enhance the bioadhesive properties of a polymer preferably are water-insoluble metal compounds, such as water-insoluble metal oxides and hydroxides, including oxides of calcium, iron, copper and zinc. The metal compounds can be incorporated within a wide range of hydrophilic and hydrophobic polymers including proteins, polysaccharides and synthetic biocompatible polymers. In one embodiment, metal oxides can be incorporated within polymers used to form or coat drug delivery devices, such as microspheres, which contain a drug or diagnostic agent. The metal compounds can be provided in the form of a fine dispersion of particles on the surface of a polymer that coats or forms the devices, which enhances the ability of the devices to bind to mucosal membranes. The polymers, for example in the form of microspheres, have improved ability to adhere to mucosal membranes, and thus can be used to deliver a drug or diagnostic agent via any of a range of mucosal membrane surfaces including those of the gastrointestinal, respiratory, excretory and reproductive tracts.

DETAILED DESCRIPTION OF THE INVENTION

Figure 1:
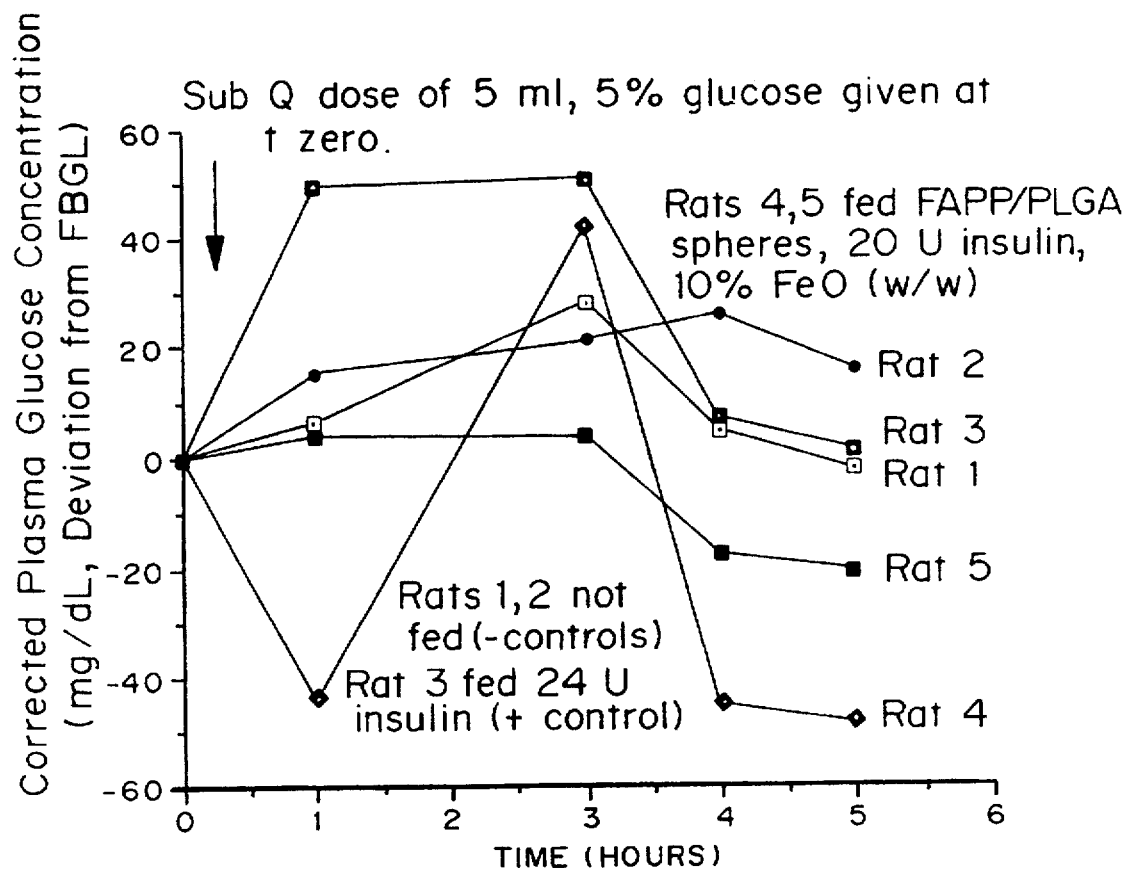
FIG. 1 is a graph comparing blood glucose levels in rats after administration of insulin in a saline solution and in poly(fumaric acid)/poly(lactide-co-glycolide) microspheres containing FeO.
Figure 1:
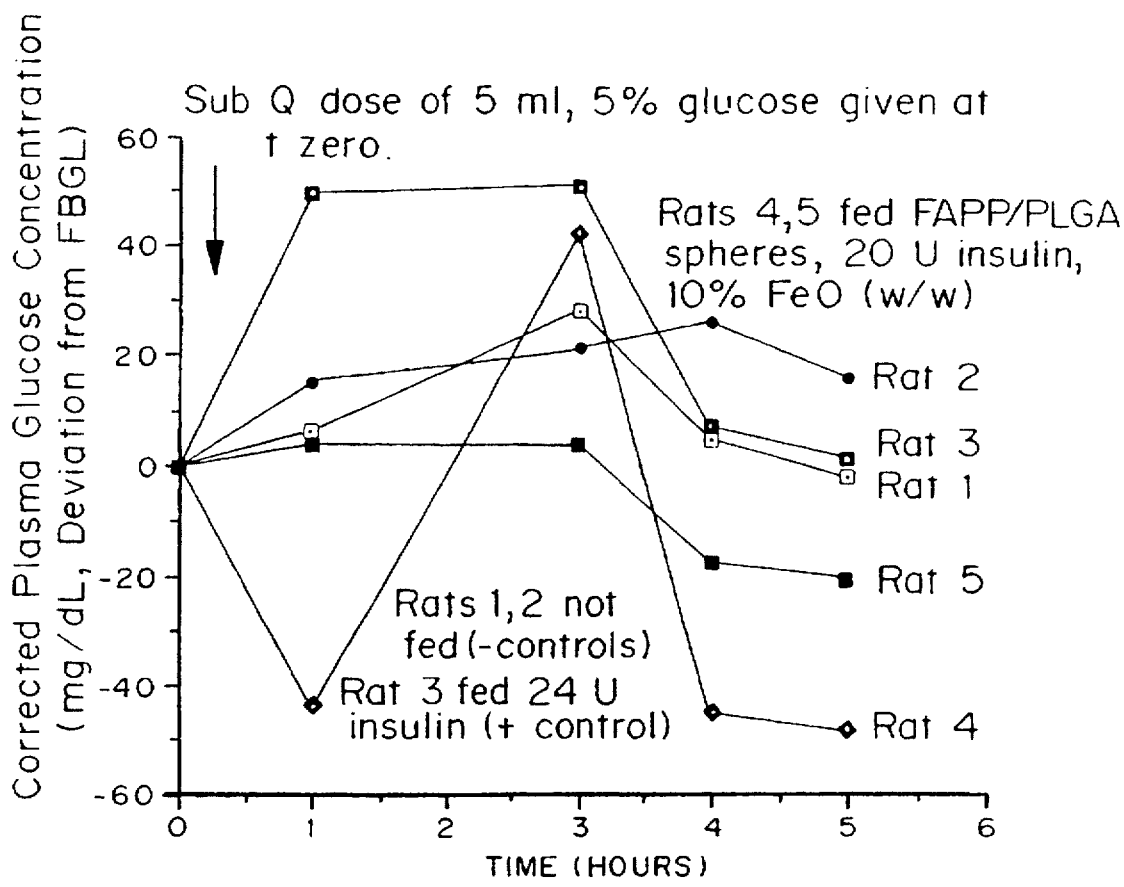

Methods and compositions are provided for enhancing the bioadhesive properties of polymers. Polymers having a metal compound incorporated therein are provided which have an improved ability to adhere to tissue surfaces, such as mucosal membranes. The metal compound incorporated into the polymer can be, for example, a water-insoluble metal oxide. In one embodiment, the polymers can be used to form drug delivery devices, such as polymeric microspheres, containing a therapeutic or diagnostic agent. The incorporation of metal compounds into a wide range of different polymers which are not normally bioadhesive dramatically improves their ability to adhere to tissue surfaces such as mucosal membranes. The polymers incorporating a metal compound can be used to form a wide variety of drug delivery devices, such as polymeric microspheres, which can be used to deliver therapeutic and diagnostic agents to mucosal membranes throughout the body including the gastrointestinal, respiratory and reproductive tracts. The metal compound can be incorporated into polymers forming or coating tablets, osmotic pumps, or any device capable of interacting with mucosal membranes.

Metal Compounds

Metal compounds which can be incorporated into polymers to improve their bioadhesive properties include in a preferred embodiment water-insoluble metal compounds, such as water-insoluble metal oxides and metal hydroxides, which are capable of becoming incorporated into and associated with a polymer to thereby improve the bioadhesiveness of the polymer. As defined herein, a water-insoluble metal compound is defined as a metal compound with little or no solubility in water, for example, less than about 0.0–0.9 mg/ml.

The water-insoluble metal compounds, such as metal oxides, can be incorporated by one of the following mechanisms: (a) physical mixtures which result in entrapment of the metal compound; (b) ionic interaction between metal compound and polymer; (c) surface modification of the polymers which would result in exposed metal compound on the surface; and (d) coating techniques such as fluidized bead, pan coating or any similar methods known to those skilled in the art, which produce a metal compound enriched layer on the surface of the device.

Preferred properties defining the metal compound include: (a) substantial insolubility in aqueous environments, such as acidic or basic aqueous environments (such as those present in the gastric lumen); and (b) ionizable surface charge at the pH of the aqueous environment.

The pKa for ionization of the metal compound may influence binding of the polymers under different pH conditions. Table 1 shows the acid ionization constants for certain aqua metal ions. CRC Handbook of Food Additives (T. E. Furia, Editor) 1968, Cleveland, Ohio.

TABLE 1

| Acid Ionization Constants (pKa at 25° C.) for Aqua Ions | | | | | | | | |
|---|---|---|---|---|---|---|---|---|
| $Ba^{2+}$ | $Ca^{2+}$ | $Mg^{2+}$ | $Ni^{2+}$ | $Ni^{3+}$ | $Fe^{2+}$ | $Cu^{2+}$ | $Al^{3+}$ | $Fe^{3+}$ |
| 13.2 | 12.6 | 11.4 | 10.6 | 9.7 | 8.3 | 8.0 | 4.9 | 2.2 |

The water-insoluble metal compounds can be derived from metals including calcium, iron, copper, zinc, cadmium, zirconium and titanium. For example, a variety of water-insoluble metal oxide powders may be used to improve the bioadhesive properties of polymers such as ferric oxide, zinc oxide, titanium oxide, copper oxide, barium hydroxide, stannic oxide, aluminum oxide, nickel oxide, zirconium oxide and cadmium oxide. The incorporation of water-insoluble metal compounds such as ferric oxide, copper oxide and zinc oxide can tremendously improve adhesion of the polymer to tissue surfaces such as mucosal membranes, for example in the gastrointestinal system. The polymers incorporating a metal compound thus can be used to form or coat drug delivery devices to improve their bioadhesive properties.

In one embodiment, the metal compound is provided as a fine particulate dispersion of a water-insoluble metal oxide which is incorporated throughout the polymer or at least on the surface of the polymer which is to be adhered to a tissue surface. For example, in one embodiment, water-insoluble metal oxide particles are incorporated into a polymer defining or coating a microsphere or microcapsule used for drug delivery. In a preferred embodiment, the metal oxide is present as a fine particulate dispersion on the surface of the microsphere. The metal compound also can be incorporated in an inner layer of the polymeric device and exposed only after degradation or else dissolution of a "protective" outer layer. For example, a core particle containing drug and metal may be covered with an enteric coating designed to dissolve when exposed to gastric fluid. The metal compound-enriched core then is exposed and become available for binding to GI mucosa.

The fine metal oxide particles can be produced for example by micronizing a metal oxide by mortar and pestle treatment to produce particles ranging in size, for example from 10.0–300 nm. The metal oxide particles can be incorporated into the polymer, for example, by dissolving or dispersing the particles into a solution or dispersion of the polymer prior to microcapsule formation, and then can be incorporated into the polymer during microcapsule formation using a procedure for forming microcapsules such as one of those described in detail below. The incorporation of metal oxide particles on the surface of the microsphere advantageously enhances the ability of the of the microsphere to bind to mucosal membranes or other tissue surfaces and improves the drug delivery properties of the microsphere.

Advantageously, metal compounds which are incorporated into polymers to improve their bioadhesive properties can be metal compounds which are already approved by the FDA as either food or pharmaceutical additives, such as zinc oxide. While not being limited to any theory, it is possible that the mechanism by which the metal compounds promote adhesion may involve the ionic interaction of partially-ionized divalent or trivalent cations on the surface of the metal particles to negatively-charged molecules on tissue surfaces such as the glycosubstances found in the mucus including sialic acids.

Tissue Binding

The incorporation of metal compounds into a wide range of polymers significantly increases bioadhesion of the polymers to tissue surfaces, including mucosal membrane surfaces. The metal compound-containing polymers actively bind to non-mucosal tissues and substances including mesentery, connective tissue and fatty tissue (see Example 7).

In a preferred embodiment, water-insoluble metal compounds can be incorporated into polymers to enhance adhesion of the polymers to mucosal membranes present throughout the gastrointestinal, respiratory, excretory and reproductive tracts. Polymers incorporating water-insoluble metal compounds bind tenaciously to mucus membranes. The polymers incorporating a water-insoluble metal compound thus can be used to form polymeric drug delivery devices for delivery of a drug via a particular mucosal membrane in the body. In a preferred embodiment, polymers incorporating a water-insoluble metal oxide are provided which are used to form or coat a drug delivery device such as a polymeric microsphere for delivery of a therapeutic or diagnostic agent via gastrointestinal mucosa.

The intestinal mucosa is formed of a continuous sheet of epithelial cells of absorptive and mucin-secreting cells. Overlying the mucosa is a discontinuous protective coating, the mucus, which is made of more than 95% water, as well as electrolytes, proteins, lipids and glycoproteins. The glycoproteins are responsible for the gel-like characteristics of the mucus. These glycoproteins consist of a protein core with covalently attached carbohydrate chains terminating in either sialic acid or L-fucose groups. The mucous glycoproteins act as "dummy receptors" for carbohydrate binding ligands which have evolved in nature to allow microorganisms and parasites to establish themselves on the gut wall. One function of the mucus is to intercept these ligands and associated ineffective agents and thereby protect the mucosa.

While not being limited to any theory, it is possible that the enhanced binding of the polymers incorporating a metal compound is due to the presence of partially ionized metal compounds, such as divalent or trivalent cations, on the surface of the polymer which interact, for example, via an ionic binding attraction with negatively charged glycosubstances such as sialic acid and L-fucose groups on the mucosal membrane surface. Multivalent ions such as divalent or trivalent cations in the metal compounds generally have the strongest affinity for the negatively-charged mucin chains.

Polymers

Metal compounds can be incorporated into a wide range of different polymers to improve the ability of the polymers to bind to tissue. For example, water-insoluble metal compounds such as water-insoluble metal oxides can be incorporated into polymers used to form or coat drug delivery devices such as polymeric microspheres. Suitable polymers which can be used, into which the metal compounds can be incorporated, include soluble and water-insoluble, and biodegradable and nonbiodegradable polymers, including hydrogels, thermoplastics, and homopolymers, copolymers and blends of natural and synthetic polymers.

Representative polymers which can be used include hydrophilic polymers, such as those containing carboxylic groups, including polyacrylic acid. Bioerodible polymers including polyanhydrides, poly(hydroxy acids) and polyesters, as well as blends and copolymers thereof also can be used. Representative bioerodible poly(hydroxy acids) and copolymers thereof which can be used include poly (lactic acid), poly(glycolic acid), poly(hydroxy-butyric acid), poly(hydroxyvaleric acid), poly(caprolactone), poly (lactide-co-caprolactone), and poly(lactide-co-glycolide). Polymers containing labile bonds, such as polyanhydrides and polyorthoesters, can be used optionally in a modified form with reduced hydrolytic reactivity. Positively charged hydrogels, such as chitosan, and thermoplastic polymers, such as polystyrene also can be used.

Representative natural polymers which also can be used include proteins, such as zein, modified zein, casein, gelatin, gluten, serum albumin, or collagen, and polysaccharides such as dextrans, polyhyaluronic acid and alginic acid. Representative synthetic polymers include polyphosphazenes, polyamides, polycarbonates, polyacrylamides, polysiloxanes, polyurethanes and copolymers thereof. Celluloses also can be used. As defined herein the term "celluloses" includes naturally occurring and synthetic celluloses, such as alkyl celluloses, cellulose ethers, cellulose esters, hydroxyalkyl celluloses and nitrocelluloses. Exemplary celluloses include ethyl cellulose, methyl cellulose, carboxymethyl cellulose, hydroxymethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, cellulose triacetate and cellulose sulfate sodium salt.

Polymers of acrylic and methacrylic acids or esters and copolymers thereof can be used. Representative polymers which can be used include poly(methyl methacrylate), poly (ethyl methacrylate), poly(butyl methacrylate), poly (isobutyl methacrylate), poly(hexyl methacrylate), poly (isodecyl methacrylate), poly(lauryl methacrylate), poly (phenyl methacrylate), poly(methyl acrylate), poly (isopropyl acrylate), poly(isobutyl acrylate), and poly (octadecyl acrylate).

Other polymers which can be used include polyalkylenes such as polyethylene and polypropylene; polyarylalkylenes such as polystyrene; poly(alkylene glycols), such as poly (ethylene glycol); poly(alkylene oxides), such as poly (ethylene oxide); and poly(alkylene terephthalates), such as poly(ethylene terephthalate). Additionally, polyvinyl polymers can be used, which, as defined herein includes polyvinyl alcohols, polyvinyl ethers, polyvinyl esters and polyvinyl halides. Exemplary polyvinyl polymers include poly (vinyl acetate), polyvinyl phenol and polyvinylpyrrolidone.

Polymers which alter viscosity as a function of temperature or shear or other physical forces also may be used. Poly(oxyalkylene) polymers and copolymers such as poly (ethylene oxide)-poly(propylene oxide) (PEO-PPO) or poly (ethylene oxide)-poly(butylene oxide) (PEO-PBO) copolymers, and copolymers and blends of these polymers with polymers such as poly(alpha-hydroxy acids), including but not limited to lactic, glycolic and hydroxybutyric acids, polycaprolactones, and polyvalerolactones, can be synthesized or commercially obtained. For example, polyoxyalkylene copolymers are described in U.S. Pat. Nos. 3,829,506; 3,535,307; 3,036,118; 2,979,578; 2,677,700; and 2,675,619, the teachings of which are incorporated herein.

Polyoxyalkylene copolymers are sold, for example, by BASF under the tradename Pluronics™. These materials are applied as viscous solutions at room temperature or lower which solidify at the higher body temperature. Other materials with this behavior are known in the art, and can be utilized as described herein. These include Kluce™ (hydroxypropyl cellulose), and purified konjac glucomannan gum.

Polymer solutions that are liquid at an elevated temperature but solid or gelled at body temperature can also be utilized. A variety of thermoreversible polymers are known, including natural gel-forming materials such as agarose, agar, furcellaran, beta-carrageenan, beta-1,3-glucans such as curdlan, gelatin, or polyoxyalkylene containing compounds, as described above. Specific examples include thermosetting biodegradable polymers for in vivo use described in U.S. Pat. No. 4,938,763 to Dunn, et al., the teachings of which are incorporated herein.

These polymers can be obtained from sources such as Sigma Chemical Co., St. Louis, Mo: Polysciences, Warrenton, Pa.; Aldrich, Milwaukee, Wis.; Fluka, Ronkonkoma, N.Y.; and BioRad, Richmond, Calif., or can be synthesized from monomers obtained from these or other suppliers using standard techniques.

Formation of Polymeric Microspheres

A wide variety of polymers can be used to form microspheres, wherein the polymer surface of the microsphere has incorporated therein a metal compound which enhances bioadhesive properties of the microsphere such as the ability of the microsphere to adhere to mucosal membranes. The metal compounds, such as water-insoluble metal oxides, which enhance the bioadhesive properties of the polymers preferably are incorporated into the polymer before formation of the microspheres. As used herein, the term "microspheres" includes microparticles and microcapsules having a core of a different material than the outer wall. Generally, the microspheres have a diameter from the nanometer range up to about 5 mm. The microsphere may consist entirely of bioadhesive polymer incorporating a metal compound such as a water-insoluble metal oxide or can have only an outer coating of bioadhesive polymer incorporating the metal compound.

In one embodiment, polylactic acid microspheres can be fabricated using methods including solvent evaporation, hot-melt microencapsulation and spray drying. Polyanhydrides made of bis-carboxyphenoxypropane and sebacic acid or poly(fumaric-co-sebacic) can be prepared by hot-melt microencapsulation. Polystyrene microspheres can be prepared by solvent evaporation. Hydrogel microspheres can be prepared by dripping a polymer solution, such as alginate, chitosan, alginate/polyethylenimine (PEI) and carboxymethyl cellulose (CMC), from a reservoir though microdroplet forming device into a stirred ionic bath, as disclosed in PCT WO 93/21906, published Nov. 11, 1993, the disclosure of which is incorporated herein by reference.

One or more metal compounds can be incorporated into the polymeric microspheres either before or after formation. For example, water-insoluble metal compounds, such as a water-insoluble metal oxide, can be incorporated into the microspheres by combining a finely ground dispersion of particles of metal oxide in a solution or dispersion with the polymer before forming the microsphere via methods such as those described below. Alternatively, the metal compound can be incorporated into the polymer after formation of the microsphere, for example by dispersing the microsphere in a solution or dispersion of the metal compound and then removing the solvent by evaporation or filtration. The metal compound can become incorporated into the polymer for example by ionic interactions. It is only necessary that the metal compound be incorporated into the surface of the microcapsule to enable the metal compound to promote bioadhesion of the microcapsule to tissue surfaces such as mucosal membrane surfaces, or that degradation, dissolution or swelling of the outer layers can occur to expose the metal compound over time.

A. Solvent Evaporation

Methods for forming microspheres using solvent evaporation techniques are described in E. Mathiowitz et al., *J. Scanning Microscopy*, 4:329 (1990); L. R. Beck et al., *Fertil. Steril.*, 31:545 (1979); and S. Benita et al., *J. Pharm. Sci.*, 73:1721 (1984), the disclosures of which are incorporated herein by reference. The polymer is dissolved in a volatile organic solvent, such as methylene chloride. A substance to be incorporated is added to the solution, and the mixture is suspended in an aqueous solution that contains a surface active agent such as poly(vinyl alcohol). The resulting emulsion is stirred until most of the organic solvent evaporated, leaving solid microspheres. Microspheres with different sizes (1–1000 microns) and morphologies can be obtained by this method. This method is useful for relatively stable polymers like polyesters and polystyrene. However, labile polymers, such as polyanhydrides, may degrade during the fabrication process due to the presence of water. For these polymers, some of the following methods performed in completely anhydrous organic solvents are more useful.

B. Hot Melt Microencapsulation

Microspheres can be formed from polymers such as polyesters and polyanhydrides using hot melt microencapsulation methods as described in Mathiowitz et al., *Reactive Polymers*, 6:275 (1987), the disclosure of which is incorporated herein by reference. In this method, the use of polymers with molecular weights between 3–75,000 daltons is preferred. In this method, the polymer first is melted and then mixed with the solid particles of a substance to be incorporated that have been sieved to less than 50 microns. The mixture is suspended in a non-miscible solvent (like silicon oil), and, with continuous stirring, heated to 5° C. above the melting point of the polymer. Once the emulsion is stabilized, it is cooled until the polymer particles solidify. The resulting microspheres are washed by decantation with petroleum ether to give a free-flowing powder. Microspheres with sizes between one to 1000 microns are obtained with this method.

C. Solvent Extraction

This technique is primarily designed for polyanhydrides and is described, for example, in PCT WO 93/21906, published Nov. 11, 1993, the disclosure of which is incorporated herein by reference. In this method, the substance to be incorporated is dispersed or dissolved in a solution of the selected polymer in a volatile organic solvent like methylene chloride. This mixture is suspended by stirring in an organic oil, such as silicon oil, to form an emulsion. Microspheres that range between 1–300 microns can be obtained by this procedure.

D. Spray-Drying

Methods for forming microspheres using spray drying techniques are described in U.S. Ser. No 08/467,811, filed Aug. 7, 1995, the disclosure of which is incorporated by reference. In this method, the polymer is dissolved in an organic solvent such as methylene chloride. A known amount of a substance to be incorporated is suspended (insoluble agent) or co-dissolved (soluble agent) in the polymer solution. The solution or the dispersion then is spray-dried. Microspheres ranging between 1–10 microns are obtained. This method is useful for preparing microspheres for imaging of the intestinal tract. Using the method, in addition to metal compounds, diagnostic imaging agents such as gases can be incorporated into the microspheres.

E. Phase Inversion

Microspheres can be formed from polymers using a phase inversion method wherein a polymer is dissolved in a good solvent, fine particles of a substance to be incorporated, such as a drug, are mixed or dissolved in the polymer solution, and the mixture is poured into a strong non-solvent for the polymer, to spontaneously produce, under favorable conditions, polymeric microspheres, wherein the polymer is either coated on the particles or the particles are dispersed in the polymer. The method can be used to produce microparticles in a wide range of sizes, including, for example, about 100 nanometers to about 10 microns. Exemplary polymers which can be used include polyvinylphenol and polylactic acid. Substances which can be incorporated include, for example, imaging agents such as fluorescent dyes, or biologically active molecules such as proteins or nucleic acids.

F. Protein Microencapsulation

Protein microspheres can be formed by phase separation in a non-solvent followed by solvent removal as described in U.S. Pat. No. 5,271,961 to Mathiowitz et al., the disclosure of which is incorporated herein by reference. Proteins which can be used include prolamines such as zein. Additionally, mixtures of proteins or a mixture of proteins and a bioerodable material polymeric material such as a polylactide can be used. In one embodiment, a prolamine solution and a substance to be incorporated are contacted with a second liquid of limited miscibility with the proline solvent, and the mixture is agitated to form a dispersion. The prolamine solvent then is removed to produce stable prolamine microspheres without crosslinking or heat denaturation. Other prolamines which can be used include gliadin, hordein and kafirin. Substances which can be incorporated in the microspheres include, in addition to the metal compound, pharmaceuticals, pesticides, nutrients and imaging agents.

G. Low Temperature Casting of Microspheres

Methods for very low temperature casting of controlled release microspheres are described in U.S. Pat. No. 5,019,400 to Gombotz et al., the disclosure of which is incorporated herein by reference. In the method, a polymer is dissolved in a solvent together with a dissolved or dispersed substance to be incorporated, and the mixture is atomized into a vessel containing a liquid non-solvent at a temperature below the freezing point of the polymer-substance solution, which freezes the polymer droplets. As the droplets and non-solvent for the polymer are warmed, the solvent in the droplets thaws and is extracted into the non-solvent, resulting in the hardening of the microspheres.

In addition to the metal compound, biological agents such as proteins, short chain peptides, polysaccharides, nucleic acids, lipids, steroids, and organic and inorganic drugs can be incorporated into the microspheres. Polymers which can be used to form the microspheres include but are not limited to poly(lactic acid), poly(lactic-co-glycolic acid), poly (caprolactone), polycarbonates, polyamides and polyanhydrides. The microspheres produced by this method are generally in the range of 5 to 1000 micrometers, preferably between about 30 and 50 micrometers.

H. Double Walled Microcapsules

Methods for preparing multiwall polymer microspheres are described in U.S. Ser. No. 08/478,103, filed Jun. 7, 1995, the disclosure of which is incorporated herein by reference. In one embodiment, two hydrophilic polymers are dissolved in an aqueous solution. A substance to be incorporated is dispersed or dissolved in the polymer solution, and the mixture is suspended in a continuous phase. The solvent then is slowly evaporated, creating microspheres with an inner core formed by one polymer and an outer layer of the second polymer. The continuous phase can be either an organic oil, a volatile organic solvent, or an aqueous solution containing a third polymer that is not soluble with the first mixture of polymers and which will cause phase separation of the first two polymers as the mixture is stirred.

Multilayer polymeric drug, protein, or cell delivery devices can be prepared from two or more hydrophilic polymers using the method. Any two or more different biodegradable, or non-degradable, water soluble polymers which are not soluble in each other at a particular concentration as dictated by their phase diagrams may be used. The multilayer microcapsules have uniformly dimensioned layers of polymer and can incorporate a range of substances in addition to the metal compound including biologically active agents such as drugs or cells, or diagnostic agents such as dyes.

Microspheres containing a polymeric core made of a first polymer and a uniform coating of a second polymer, and a substance incorporated into at least one of the polymers, can be made as described in U.S. Pat. No. 4,861,627, the disclosure of which is incorporated herein by reference.

I. Hydrogel Microspheres

Microspheres made of gel-type polymers, such as alginate, are produced through traditional ionic gelation techniques. The polymer first is dissolved in an aqueous solution, mixed with a substance to be incorporated, and then extruded through a microdroplet forming device, which in some instances employs a flow of nitrogen gas to break off the droplet. A slowly stirred ionic hardening bath is positioned below the extruding device to catch the forming microdroplets. The microspheres are left to incubate in the bath for twenty to thirty minutes in order to allow sufficient time for gelation to occur. Microsphere particle size is controlled by using various size extruders or varying either the nitrogen gas or polymer solution flow rates.

Chitosan microspheres can be prepared by dissolving the polymer in acidic solution and crosslinking it with tripolyphosphate. Carboxymethyl cellulose (CMC) microspheres can be prepared by dissolving the polymer in acid solution and precipitating the microsphere with lead ions. Alginate/polyethylene imide (PEI) can be prepared in order to reduce the amount of carboxylic groups on the alginate microcapsule. The advantage of these systems is the ability to further modify their surface properties by the use of different chemistries. In the case of negatively charged polymers (e.g., alginate, CMC), positively charged ligands (e.g., polylysine, polyethyleneimine) of different molecular weights can be ionically attached.

Therapeutic and Diagnostic Agents

Polymers incorporating a metal compound which improves the bioadhesive properties of the polymer can be used to form, or to coat, drug delivery devices such as microspheres or tablets containing any of a wide range of therapeutic and diagnostic agents. The drug delivery devices can be administered by, e.g., oral, rectal, nasal or vaginal administration.

In one embodiment, the polymers incorporating a water-insoluble metal compound may be used to form bioadhesive microspheres containing a drug which is either dispersed throughout the polymer or dispersed within one or more areas within the microsphere. Any of a wide range of materials can be incorporated into the microspheres including organic compounds, inorganic compounds, proteins, polysaccharides, and nucleic acids, such as DNA, using standard techniques. Examples of useful proteins include hormones such as insulin, growth hormones including somatometins, transforming growth factors, and other growth factors, antigens for oral vaccines, enzymes such as lactase or lipases, and digestive aids such as pancreatin. The polymers incorporating the metal compound and the diagnostic or therapeutic agent also may be formulated as a tablet using methods available in the art.

The incorporation of metal compounds into polymers increases their ability to bind to mucous membranes. Thus, the incorporation of metal compounds into the polymers can enhance the adhesion of the polymers to mammalian mucous membranes including those the entire gastrointestinal tract, respiratory, excretory and reproductive tracts, and thus can enhance the delivery of drugs incorporated into the polymers. The drug delivery systems thus can be used for gastrointestinal, vaginal or respiratory delivery of a preselected drug or diagnostic agent. Polymers in the form of, for example, microspheres can be administered in a pharmaceutically acceptable carrier as, for example, a suspension or ointment to the mucosal membranes, via, e.g., the nose, mouth, rectum, or vagina. Pharmaceutically acceptable carriers for example for oral or topical administration are known and determined based on compatibility with the polymeric material. Other carriers include bulking agents such as Metamucil™.

Therapeutic or diagnostic agents which can be incorporated into microspheres or other drug delivery devices for application to the vaginal lining or other mucosal membrane lined orifices such as the rectum include spermacides, yeast or trichomonas treatments and anti-hemorrhoidal treatments. The metal compound-containing polymers can be used in any muco-adherent delivery system including gastrointestinal delivery and vaginal delivery systems. For example, the polymers incorporating a metal compound can be used to improve adhesion of vaginal rings used for delivery of contraceptives or hormones, or to improve the residence time of osmotic pumps. Microspheres also may be formulated for adhesion and delivery of chemotherapeutic agents to tumor cells.

Polymeric materials such as microspheres incorporating metal compounds which promote bioadhesiveness are useful for the oral administration of a wide range of drugs, such as sulfonamides (e.g., sulfasalazine) and glycocorticoids (e.g., bethamethasone) used for treatment of bowel diseases. Examples of other useful drugs include ulcer treatments such as Carafate™ from Marion Pharmaceuticals, neurotransmitters such as L-DOPA, antihypertensives or saluretics such as Metolazone from Searle Pharmaceuticals, carbonic anhydrase inhibitors such as Acetazolamide from Lederle Pharmaceuticals, insulin like drugs such as glyburide, a blood glucose lowering drug of the sulfonylurea class, synthetic hormones such as Android F from Brown Pharmaceuticals and Testred (methyltestosterone) from ICN Pharmaceuticals, and antiparasitics such as mebendazole (Vermox™, Jannsen Pharmaceutical), and growth factors such as fibroblast growth factor ("FGF"), platelet derived growth factor ("PDGF"), epidermal growth factor ("EGF"), and tissue growth factor-$\beta$ ("TGF-$\beta$").

Polymeric microspheres incorporating a metal compound to enhance bioadhesion, and a drug such as sulfasalazine are especially useful for treatment of inflammatory bowel diseases such as ulcerative colitis and Crohn's disease. In ulcerative colitis, inflammation is restricted to the colon, whereas in Crohn's disease, inflammatory lesions may be found throughout the gastrointestinal tract, from the mouth to the rectum. Sulfasalazine is one of the drugs that is used for treatment of these diseases. Sulfasalazine is cleaved by bacteria within the colon to sulfapyridine, an antibiotic, and to 5-amino salicylic acid, an anti-inflammatory agent. The 5-amino salicylic acid is the active drug and it is needed locally. The polymeric drug delivery systems can improve the therapy by retaining the drug for a prolonged time in the intestinal tract. For Crohn's disease, retention of 5-aminosalicylic acid in the upper intestine is of great importance, since bacteria cleave the sulfasalazin in the colon, and the usual way to treat inflammations in the upper intestine is by local administration of 5-aminosalicylic acid.

The polymeric microspheres also may be used for oral vaccines. Microspheres incorporating antigens for use as a vaccine can be fabricated to have different retention times in the gastrointestinal tract. The different retention times, among other factors, can stimulate production of more than one type (IgG, IgM, IgA, IgE, etc.) of antibody.

The size of the microspheres can be selected to optimize microsphere uptake, alone or in combination with other factors, including polymer composition. As used herein, the term "microspheres" is defined as polymeric particles or capsules having a diameter on the order of 5 mm (5000 microns) or less, including particles or capsules having a diameter less than 1 mm, in the micrometer scale, or, for example, less than 1 µm, in the nanometer scale, for example 100–1000 nanometers.

In one embodiment, microspheres with a diameter less than about 10 microns may be used. Enhanced uptake is achieved if the polymeric microspheres are loaded with metal oxide and fabricated to be smaller than 3 µ. In one embodiment, microspheres with a diameter between about 2 to 5 microns can be used, to enhance uptake into gut-associated lymphoid tissue, in particular into lymphatic cells and phagocytic cells. Additionally, microspheres less than about 2 microns, or optionally, less than about 1 micron in diameter, can be used, to enhance uptake by non-lymphatic cells and non-phagocytic cells. To reduce uptake, microspheres having a diameter greater than 10 microns can be used, for example, to enhance delivery of a drug or diagnostic agent in the microspheres to the gastrointestinal tract.

Metal compound-containing polymers also can be used to coat or form microspheres for the oral or intravenous administration of radio-opaque materials for use in imaging. In a preferred method for imaging, a radio-opaque material such as barium is coated with the polymer having the metal compound incorporated therein. Examples of other radio-opaque materials include gases or gas emitting compounds. Other radioactive materials or magnetic materials can be used in place of, or in addition to, the radio-opaque materials.

Polymers incorporating metal compounds also may be used to form or coat devices used as a perivascular treatment to prevent restenosis of blood vessels following balloon angioplasty. The metal compound-containing devices may be implanted outside damaged blood vessel walls and the bioadhesive properties used to retain the devices at the implant site and deliver anti-proliferative or thrombolytic drugs to the vessel wall, as described by E. Edelman et al., *Proc. Natl. Acad. Sci.*, USA 30:1513–1517 (1993).

The polymers incorporating a water insoluble metal compound also can be used in applications for controlled release of anti-arrhythmic agents. R. Levy et al., *J. Pharm. Sci.*, 83:156–1643 (1994) describes the use of non-bioadhesive polymeric implants attached to the heart for delivery of drugs to prevent arrthymias. Bioadhesive microspheres incorporating water-insoluble metal oxides may be used to deliver growth factors or other bioactive drugs to the heart in a site-specific manner after attachment to the pericardial sac. The delivery of bioactive drugs to the heart using alginate microspheres has been described by K. Harada et al., *J. Clin. Invest.*, 94:623–630 (1994).

Drug Delivery Devices

The bioadhesion of any of a wide range of different polymeric drug delivery devices can be enhanced by the incorporation of a water-insoluble metal compound into the polymer. In one embodiment, polymers incorporating a water-insoluble metal compound can be used to form microsphere delivery devices or used to coat pre-existing microspheres. Films, coatings and other devices also can be formed from polymers incorporating a water-insoluble metal compound to improve the bioadhesiveness of the devices. For example, a polymeric coating of a polymer incorporating a water-insoluble metal compound can be coated on controlled-release drug delivery devices ranging from micrometer sized microspheres to millimeter sized pumps such as osmotic pumps, or on delivery devices such as vaginal rings. The bioadhesiveness of the devices thus can be improved and therefore their effectiveness in drug delivery applications can be enhanced.

The films and coatings can be formed using methods available in the art, including, for example, film casting, extrusion, melt casting, pressing, molding, and coating techniques such as pan coating. In one embodiment, for example, the metal compound can be incorporated into coatings applied by fluidized beds for the coating of large tablets. The benefits of bioadhesive drug delivery devices include increased bioavailability, the protection of labile drugs from inactivation by digestive enzymes or other hydrolytic processes, and increased patient compliance because of reduced dosing regimens. Advantageously, FDA approved metal compounds such as zinc oxide can be used. In order to increase bioadhesion, the metal compound should be present on the surface of the device but still entrapped in polymer. Additionally, the loading of the metal compound must be sufficient to increase bioadhesion without disrupting the structural integrity of the device.

The invention will be further understood from the following non-limiting examples.

Example 1: Enhancement of Polymer Bioadhesive Properties By the Incorporation of Water-Insoluble Metal Oxides.

The effectiveness of metal oxides in enhancing the bioadhesive properties of the polymers was tested using a quantitative, in vitro everted intestinal sac bioassay which provides a measure of adhesion of the polymers to intestinal mucosa.

A. Preparation of microspheres.

Poly(caprylactone) (PCL) microspheres were fabricated by the solvent evaporation technique. A 10% solution of PCL (MW=76 kDa) in methylene chloride was prepared. Control PCL microspheres were prepared by stirring the polymer solution in a 0.2% (w/v) polyvinyl alcohol aqueous solution. Microspheres were stirred for 1 hr to allow solvent to evaporate, washed with distilled water, frozen and lyophilized. FeO, CuO and NiO were micronized by mortar and pestle treatment to produce particles in the size range of 100–300 nm. To make metal oxide-loaded microspheres, the metal oxide powder was dispersed in the polymer solution by mixing and probe sonication before addition to the PVA bath, and the rest of the process was performed as described for the control microspheres. Scanning electron microscopy ("SEM") observation using a Hitachi S2700 microscope of the microspheres indicated that ferric oxide and nickel oxide microspheres had the most exposed particles on the surface of the microspheres which appeared as clumps or individual particles.

Poly(acrylonitrile-vinyl chloride) (PAN-PVC) microspheres were prepared by spray-drying a 1.5% (w/v) solution of the polymer in acetone with and without ferric oxide (60% w/w). The resulting microspheres had sizes ranging from 1–20 μ. SEM indicated that the microspheres had a very high density of iron oxide exposed as cluster on the surface of the spheres as well as considerable surface texture.

B. In Vitro Assay of Bioadhesive Properties

The effectiveness of metal oxides in enhancing the bioadhesive properties of the polymeric microspheres was tested using a quantitative, in vitro everted intestinal sac bioassay, which provides a measure of adhesion of the polymers to intestinal mucosa. In the assay, intestine from a rat was washed with saline, everted and fashioned into fluid-filled sacs with a length of 3 cm. The sacs were incubated in 5 ml of physiological saline at 37° C. for 30 minutes with a 60 mg aliquot of metal oxide treated microspheres or metal oxide with rotation agitation. After 30 minutes of incubation, the quantity of unbound beads was determined gravimetrically after lyophilization and used to calculate the percentage of beads bound to intestinal mucosa. The "% bound" parameter thus was determined as an indicator of microsphere bioadhesion.

Table 1 shows the results of the in vitro assay of the bioadhesive properties of the metal oxide treated polymeric PCL and PAN-PVC microspheres. Polycaprylactone and polyacrylonitrile-vinyl chloride microspheres generally have limited bioadhesive properties in comparison to, e.g., polylactic acid spheres which have considerable bioadhesive properties. The results shown in Table 1 illustrate that even relatively low loadings of ferric oxide (13% w/w) in microspheres made of non-bioadhesive polymers, such as polycaprylactone, can greatly improve the bioadhesive properties.

TABLE 2

Bioadhesion of Polymers

| Material | Initial Dose (mg) | Bound (mg) | % Bound | Std. Err. |
|---|---|---|---|---|
| Polycaprylactone spheres (control) | 57.7 | 5.0 | 8.7 | 1.1 |
| Polycaprylactone spheres + 13% FeO (w/w) | 59.8 | 17.1 | 28.6 | 6.4 |
| Polycaprylactone spheres + 23% FeO (w/w) | 63.3 | 18.5 | 29.1 | 11.1 |
| FeO powder | 63.5 | 18.6 | 29.6 | 4.0 |
| Polycaprylactone spheres + 9.1% CuO (w/w) | 61.4 | 9.1 | 14.9 | 0.2 |
| Polycaprylactone spheres + 9.1% NiO (w/w) | 64.5 | 7.9 | 12.2 | 5.2 |

TABLE 2-continued

Bioadhesion of Polymers

| Material | Initial Dose (mg) | Bound (mg) | % Bound | Std. Err. |
|---|---|---|---|---|
| Polyacrylonitrile-vinyl chloride spheres (control) | 54.1 | 3.9 | 7.3 | 1.9 |
| Polyacrylonitrile-vinyl chloride spheres + 60% FeO (w/w) | 61.0 | 16.4 | 26.8 | 3.0 |
| Polylactic acid (134K) spheres (control) | 60.4 | 16.9 | 28.0 | 9.9 |
| Polylactic acid (134K) spheres (control) | 60.5 | 20.2 | 33.3 | 1.6 |

As illustrated in Table 2, a three-fold increase in bioadhesion was obtained for ferric oxide-loaded polycaprolactone microspheres (29% bound for the iron-loaded spheres versus 9% for the control spheres) and a 1.5-fold increase in bioadhesion was obtained for cupric oxide and nickel oxide-loaded microspheres (15% and 12% bound for the cupric oxide and nickel oxide, respectively versus 9% for the control). The unencapsulated micronized FeO powder had the same bioadhesion as the polymer spheres loaded with FeO (29%). A four-fold increase in bioadhesion was obtained for ferric oxide-loaded PAN-PVC microspheres (27% bound for the iron-loaded spheres versus 7% for the control spheres).

Example 2: Ferric Oxide Loaded Zein Microspheres

Zein (prolamine) microspheres were prepared by heat-curing an emulsified, alcoholic zein solution in a corn oil bath. The spheres were prepared either as controls or with ferric oxide loading (54.5% w/w) and were washed with petroleum ether to remove residual oil and air-dried. The resulting microspheres were in the size range of 1–30 μ. The spheres were tested using the rat everted intestinal sac bioassay described in Example 1 and the results indicated that ferric oxide increased bioadhesion two-fold (48% for ferric oxide-loaded spheres versus 28% for control spheres). SEM indicated that the zein loaded spheres had a very high density of iron clusters compared to the smooth surface morphology of the control spheres.

Example 3: Ferric Oxide Loaded Poly(Fumaric-co-Sebacic) Acid Microspheres

Poly(fumaric-co-sebacic) acid 20:80 (P(FA:SA) 20:80, 6 KDa), a polyanhydride synthesized using melt condensation of prepolymers, was fashioned into microspheres using the hot-melt technique. The polymer was melted at 80° C., mixed with ferric oxide powder to produce a 12% (w/w) loading and dispersed into silicon oil heated to 90° C. with stirring. The resulting emulsion of molten polymer in oil was hardened by cooling the system to ambient temperature and the solid spheres were recovered by filtration and washed with petroleum ether to remove oil. The spheres were sieved to a size range of 106–500 μ and tested using the rat everted intestinal sac bioassay described in Example 1. The results indicated that 44% of the initial dose of spheres adhered to small intestine. SEM indicated iron oxide was distributed evenly throughout the spheres and that ferric oxide was present on the surface in high density.

Example 4: Ferric Oxide Loaded Polystyrene Microspheres

Polystyrene (2 KDa) microspheres containing 40% ferric oxide (w/w) were prepared by solvent evaporation in the size range 10–300 μ. The microspheres were tested using the rat everted intestinal sac bioassay described in Example 1 which showed that the 38% of the initial dose of microspheres was bound to small intestine.

Example 5: Ferric Oxide-Loaded Polycaprolactone-Coated Glass Beads-In Vivo Study Glass beads (212–300 μm) were coated with a "thin" (10–50 μm) coating of polycaprolactone (PCL) containing ferric oxide using a "dip-phase inversion" method. Briefly, 300 mg of beads were immersed for 10 sec in 5 ml of 20% PCL solution in methylene chloride (w/v, MW=76 kDa) containing micronized ferric oxide at a loading of 16.7% (w/w of polymer) and subsequently drained of the polymer solution. The beads were rinsed in 20 ml of petroleum ether, a non-solvent for the polymer solution (with miscibility in methylene chloride), briefly agitated by shaking and bath sonication for 30 sec, drained and air dried. As methylene chloride leaves the viscous polymer solution adherent to the glass spheres and enters the non-solvent (petroleum ether), PCL precipitates as a continuous coating on the glass spheres through the mechanism of "phase inversion".

200 mg of the coated beads were resuspended in 1.5 ml of saline and fed by stomach tube to a 400 g, unfasted rat that had been lightly anaesthetized with Metofane (Methoxyflurane, manufactured by Pitman-Moore, Mundelein, Ill.). The animal was sacrificed after 2.5 hrs and the entire GI tract was excised and examined. Nearly 90% of the initial dose was localized to the stomach, mixed in the stomach contents. After removal of the contents, it was observed that many spheres were in intimate contact with the mucosal lining of the stomach and that the polymer coating containing metal oxide remained intact. Isolated groups of spheres were found in the jejunum, mostly as clumps buried in mucus and intestinal contents, but still in close apposition to the mucosa, nonetheless. No spheres were found in the lower GI tract, distal to the ileum.

Example 6: Ferric Oxide Loaded Zein Microspheres In-Vivo Study

A 400 g unfasted rat was anaesthetized with Metofane and fed 100 mg of zein microspheres containing 55% ferric oxide (w/w) suspended in 1.0 ml of saline by stomach tube. The animal was sacrificed after 22 hrs and the entire GI tract was excised and examined. The particles were observed, buried in mucus and intestinal contents, throughout the entire length of the GI tract. Many spheres were in intimate contact with the mucosal epithelium. Histological examination revealed that the spheres were in contact with cells on the villous tips.

Example 7: Adhesion of Microspheres to Segments of Pig Aorta In Vitro

Small segments of pig aorta (1.5 cm×1.5 mm) were slit open and incubated with 50–60 mg of microsphere samples including different polymers or coatings containing metal oxides. The samples were made using the methods described in Examples 1 and 5. The results of the assay are shown below in Table 3.

TABLE 3

Microsphere Adhesion

| Sample | Initial Dose, mg | Bound, mg | % Bound |
|---|---|---|---|
| 10% PCL 76 kDa-Solvent Evaporation (no metal) | 60.6 | 5.7 | 9.4 |
| 10% PCL 76 kDa-Solvent Evaporation w/13% FeO (w/w) | 56.6 | 8.3 | 14.7 |
| Glass beads (500–600μ) coated with 20% PCL w/16.7% CuO (w/w) | 49.2 | 46.7 | 94.9 |
| Spray-dried PAN-PVC (0.1–20μ with 60% FeO (w/w) | 57.1 | 21.4 | 37.5 |

Of all the formulations tested, only the spray-dried PAN-PVC containing 60% FeO (w/w) showed adherence to the lumenal surface of the blood vessel and the degree of adhesion was minimal. The adhesion of the metal-loaded microspheres was primarily to the adventitia of the blood vessels, connective tissue, mesentery and fatty tissue attached to the exterior of the aorta. Nine percent of the initial dose of PCL microspheres adhered to the vessels. The addition of FeO to the spheres (13% w/w) increased the adhesion to 15 percent of the initial dose. Inclusion of 20% CuO in PCL microspheres did not significantly improve bioadhesion, and SEM analysis indicated that no CuO particles were present on the surface of the spheres. To increase the amount of CuO on the surface of spheres, glass microspheres were coated with a PCL coating containing 17% (w/w) of CuO, and the binding increased to 95% of the initial dose of spheres. Spray-dried PAN-PVC with 60% FeO (w/w) showed 38% binding, and the surface of the microspheres was very rough.

Example 8: Transmission Electron Microscopic (TEM) Visualization of Ferric-Oxide Loaded Microspheres Uptake by GI Mucosa after Oral Feeding Polystyrene (PS) microspheres containing ferric oxide were prepared by solvent evaporation. Briefly, a 20% PS solution in methylene chloride (w/v, MW=2 kDa) containing a 30% loading (w/polymer weight) of micronized ferric oxide was poured into 1L of a stirred solution of 0.5% poly(vinyl alcohol) (PVA, MW=30–70 kDa) and dispersed using a combination of Virtis Rotor-shear stirring (20K rpm with flat blade assembly) and probe sonication to produce microspheres smaller than 10 μm. The particles were "washed" with distilled water to remove PVA and collected by centrifugation.

Approximately 50 mg of the microparticles in 1 ml of saline were fed by stomach tube to a Metofane-anaesthetized, 800 gm, unfasted rat. The animal was sacrificed after 1 hr and segments of the small intestine were removed and prepared for TEM. Thin sections (80–90 nm) of the expoxy-embedded tissue were microtomed with a diamond knife and examined with and without uranyl acetate-lead citrate staining at an accelerating voltage of 100 kV with a Philips EM 410 TEM.

Iron-loaded microparticles were observed throughout the small intestine both in the lumen and the absorptive mucosa. Many microspheres were seen in close contact with the microvilli, but surprisingly many spheres were observed inside intestinal absorptive cells and penetrating between junctions of adjacent cells. The spheres observed in the cytoplasm of the absorptive cells ranged between 30 and 300 nm and were distributed: (1) below the terminal web of the microvilli, occasionally observed in pinocytotic vesicles; (2) throughout the supranuclear region localized within membranous profiles of the endoplasmic reticulum (ER) and Golgi apparatus; (3) near the lateral membranes at the level of the nucleus. The spheres were not observed in the cytoplasm beneath the nucleus at the base of the cell. It was not uncommon to visualize at least 100–200 spheres in a TEM micrograph of a single absorptive cell, representing one plane of section.

Additionally, larger microspheres (exceeding 1 μm) were often observed inside goblet cells lining the intestinal villi. The spheres were either inside mucin droplets (for "full" goblet cells) or else in the cytoplasm of goblet cells that had discharged their secretions ("empty" goblet cells).

Example 9: Insulin Delivery in Nanoparticles Produced by Phase Inverson

Nanoparticles were produced by a phase inversion process.

Fumaric acid was purchased from Fisher Chemical, and recrystallized once from a 5% solution in 95% ethanol. The fumaric acid was polymerized by refluxing for about 3.5 hr in acetic anhydride (20 g per 250 mL). After reflux, the excess acetic anhydride was removed by evaporation under vacuum, and stored at 4° C. overnight. Excess liquid acetic acid was removed via filtration if necessary, and the retentate was purified by dissolving in toluene with heat. The resulting solution then was filtered while warm, and the retentate discarded. The filtrate was allowed to crystallize at 40° C. overnight, and then washed with ether two times to remove any remaining toluene. The fumaric acid polymer precipitate was collected by filtration, dried under vacuum, and stored at −20° C. in a sealed amber glass jar.

Subsequently, 0.1 g of the polymerized fumaric acid and 0.2 g of poly(lactide-co-glycolide) (PLGA, 50:50) were dissolved in 10 mL methylene chloride. 0.022 grams of micronized FeO were added to the polymer solution.

20 mg of zinc-insulin (U.S. Biochemicals) was added to 1.0 ml of 100 mM Tris, pH 10.0, 0.25 ml of 0.3 N HCl was added to dissolve the insulin, resulting in a solution with a pH of 5.5, and an additional 0.75 ml deionized water was added to this solution, which remained clear. The final insulin concentration was 10 mg/mL. 50 μl of 10% $ZnSO_4$ was added to 0.5 mL of the insulin solution, causing crystals to form.

The zinc-insulin suspension then was added to the polymer solution and Virtis-sheared at the highest setting causing an emulsion to form. This emulsion was quickly dropped into 1L of bath sonicated petroleum ether, and allowed to sit for 15 minutes. The nanospheres were collected by vacuum filtration, air dried, frozen with liquid nitrogen and lyophilized for 24 hours. The FeO in the resulting P(FA)/PLGA microspheres also provided an electron dense tracer for Transmission Electron Microscopic ("TEM") visualization.

The use of P(FA)/PLGA nanospheres permitted insulin release to extend over three days. An in vitro release study of nanospheres loaded with 1.6% insulin (w/w) showed that 60% of insulin was released within 2 hours, and that 95% was released within 72 hours. To insure that the encapsulated insulin was not deactivated by the fabrication processing, 25 mg of the nanospheres were I.P. injected in PBS into two, fasted 300 g rats, and blood samples from the rat tail vein were tested at 1.5, 4 and 6 hrs post injection. The average fasting blood glucose level was 87±0.5 mg/dL. After 1.5 hrs the level fell to 48±2 mg/dL, after 4 hrs the level was 8±0.5 mg/dL, and after 6 hrs, the level increased to 38±14 mg/dL.

In Vivo Study

The delivery of insulin after administration of the nanoparticles, loaded with 10% w/w FeO, was studied in a rat model. Five 300 g fasted rats were anaesthetized with Metofane and fed the following formulations by stomach tube:

Rats 1 and 2: 0.5 mL saline

Rat 3: 24 I.U. insulin/0.5 mL saline (amorphous suspension)

Rats 4 and 5: 50 mg P(FA)/PLGA nanospheres containing 20 I.U. insulin and 10% w/w FeO Blood samples from the tail vein were taken as an initial baseline and rats were subsequently tested for glucose tolerance following injection of a subcutaneous glucose load, consisting of 5 mL of 5% sterile glucose solution. Tutwiler et al., *Diabetes*, 27:856–867 (1978). At 1, 3, 4 and 5 hours postfeeding, blood samples were again taken and plasma glucose levels were measured spectrophotometrically at 505 nm using the Trinder glucose assay. The glucose levels normalized to fasting blood glucose baseline levels over time are shown in FIG. 1.

The negative controls, rats 1 and 2, showed expected responses to the glucose load. Blood glucose levels rose by 35% and 31 % and then began dropping back to baseline. Rat number 3, which received an oral insulin solution, showed a greater increase in serum glucose level (62% by 3 hours) and then also returned to baseline indicating some very limited bioavailability of unencapsulated insulin.

Rat 5 had only a 4% increase in blood sugar by 3 hours and then the glucose levels dropped to below baseline. Rat 4 had very high fasting glucose level and also had very erratic measured blood levels and died after 5 hours.

The rats fed insulin-loaded nanospheres appeared to be better able to control a glucose load than the rats not given the nanospheres (4% increase at hours as opposed to ~30% increase), thus implying uptake and activity of the encapsulated insulin. Additionally, at 5 hours, only the rats fed the insulin spheres showed blood glucose levels significantly below baseline fasting levels.

Light microscopic examination of tissue samples from Rat 4 taken after 5 hrs demonstrated a widespread distribution of insulin-loaded nanospheres. The spheres were observed in great numbers, traversing the mucosal epithelium in the small intestine, Peyers' Patches ("PP"), lamina propria, lacteals, blood vessels of the gut wall and also in spleen and tissue samples.

Modifications and variations of the present invention will be obvious to those skilled in the art from the foregoing detailed description. Such modifications and variations are intended to come within the scope of the following claims.

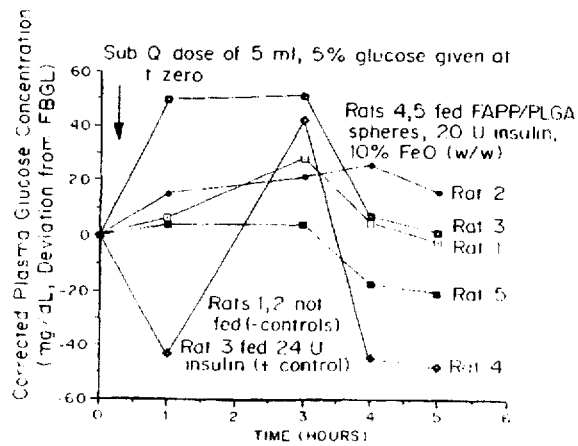

We claim:

1. A method for improving the bioadhesiveness of a polymer, the method comprising incorporating a water-insoluble metal compound in the polymer to allow for exposure of the metal compound at a surface of the polymer, thereby to enhance the ability of the polymer to adhere to a mucosal membrane, wherein the metal compound is derived from a metal selected from the group consisting of aluminum, tin, calcium, iron, copper, zinc, zirconium, nickel, and titanium, and wherein the polymer is selected from the group consisting of proteins, polysaccharides, polyamides, pplycarbonates, polyalkylenes, polyaryalkylenes, polyalkylene glycols, polyalkylene oxides, polyalkylene terephthalates, polyvinyl polymers, polyphosphazenes, polyacrylamides, polysiloxanes, polyurethanes, polymers of acrylic and methacryic acid, celluloses, polyanhydrides, polyesters, poly(hydroxy acids), and blends and copolymers of these polymers.

2. The method of claim 1 wherein the metal compound is associated with the polymer by ionic interactions.

3. The method of claim 1 wherein the polymer is in the form of a microsphere, and wherein the method comprises improving the bioadhesiveness of the microsphere by incorporating a water-insoluble metal compound in the polymer during formation of the microsphere, thereby to enhance the ability of the microsphere to adhere to a mucosal membrane.

4. The method of claim 3 wherein the metal compound is in the form of a fine dispersion of metal oxide particles on at least the surface of the microsphere.

5. The method of claim 4 wherein the metal oxide is selected from the group consisting of ferric oxide, zinc oxide, titanium oxide, copper oxide, stannic oxide, aluminum oxide, nickel oxide, and zirconium oxide.

6. The method of claim 3 wherein the polymer incorporating the metal compound is coated onto the surface of a microsphere formed of a different material.

7. The method of claim 3 wherein the microsphere further comprises a therapeutic or diagnostic agent.

8. The method of claim 7 wherein the diagnostic agent is selected from the group consisting of gases, gas evolving agents and radio-opaque compounds.

9. The method of claim 1 wherein the polymer defines or coats a drug delivery device containing a therapeutic agent.

10. The method of claim 1 wherein the polymer defines or coats a surgical implant device.

11. The method of claim 1 wherein the microsphere has a diameter greater than or equal to about 10 microns.

12. The method of claim 1 wherein the microsphere has a diameter between about 2 and 5 microns.

13. The method of claim 1 wherein the microsphere has a diameter of less than about 2 microns.

14. The method of claim 1 wherein the microsphere has a diameter less than about 1 micron.

15. The method of claim 1 wherein the metal compound is selected from the group consisting of a water-insoluble metal oxide and a water-insoluble metal hydroxide.

* * * * *

UNITED STATES PATENT AND TRADEMARK OFFICE
CERTIFICATE OF CORRECTION

PATENT : 5,985,312   Page 1 of 3

DATED : Nov. 16, 1999

INVENTOR(S) : Jules S. Jacob, et al.

It is certified that error appears in the above-identified patent and that said Letters Patent is hereby corrected as shown below:

On the title page, item [45], "Apr. 20, 1999" should read --Nov. 16, 1999--, as shown on the attached title page.

Delete the 1 Drawing Sheet and substitute therefor the attached 1 Drawing Sheet.

Signed and Sealed this

First Day of February, 2000

*Attest:*

Q. TODD DICKINSON

*Attesting Officer*   Acting Commissioner of Patents and Trademarks

United States Patent [19]

Jacob et al.

[11] Patent Number: 5,985,312
[45] Date of Patent: Nov. 16, 1999

[54] METHODS AND COMPOSITIONS FOR ENHANCING THE BIOADHESIVE PROPERTIES OF POLYMERS

[75] Inventors: Jules S. Jacob, Taunton; Edith Mathiowitz, Brookline, both of Mass.

[73] Assignee: Brown University Research Foundation, Providence, R.I.

[21] Appl. No.: 08/592,565

[22] Filed: Jan. 26, 1996

[51] Int. Cl.⁶ .......................... A61K 9/14; A61K 15/54; A61K 51/00; A61K 47/02
[52] U.S. Cl. ..................... 424/434; 424/489; 424/9.3
[58] Field of Search ....................... 424/9.1, 9.3, 111, 424/434

[56] References Cited

U.S. PATENT DOCUMENTS

| | | | |
|---|---|---|---|
| 2,675,619 | 6/1954 | Cone | 33/76 |
| 2,677,700 | 5/1954 | Jackson et al. | 260/488 |
| 2,979,578 | 4/1961 | Curtis et al. | 200/32 |
| 3,036,118 | 5/1962 | Jackson et al. | 260/484 |
| 3,535,307 | 10/1970 | Moss et al. | 260/209 |
| 3,829,506 | 8/1974 | Schmolka et al. | 260/615 |
| 4,861,627 | 8/1989 | Mathiowitz et al. | 427/213.31 |
| 4,938,763 | 7/1990 | Dunn et al. | 604/891.1 |
| 4,976,968 | 12/1990 | Steiner | 424/491 |
| 5,019,400 | 5/1991 | Gombotz et al. | 424/497 |
| 5,213,788 | 5/1993 | Ranney | 424/9 |
| 5,219,554 | 6/1993 | Groman et al. | 424/9 |
| 5,271,961 | 12/1993 | Mathiowitz et al. | 427/213.31 |
| 5,427,767 | 6/1995 | Kresse et al. | 424/9.32 |
| 5,498,421 | 3/1996 | Grinstaff et al. | 424/9.3 |
| 5,527,321 | 6/1996 | Unger | 424/9.3 |
| 5,547,682 | 8/1996 | Chagnon et al. | 424/497 |

FOREIGN PATENT DOCUMENTS

| | | |
|---|---|---|
| 0 200 508 A2 | 12/1986 | European Pat. Off. |
| 0 333 523 A2 | 3/1989 | European Pat. Off. |
| 0 363 224 A1 | 4/1990 | European Pat. Off. |
| 0 526 862 A1 | 2/1993 | European Pat. Off. |
| 0 625 353 A1 | 11/1994 | European Pat. Off. |
| 44 34 929 A1 | 1/1996 | Germany |
| WO 91/06286 | 5/1991 | WIPO |
| WO 91/06287 | 5/1991 | WIPO |
| WO 91/14733 | 10/1991 | WIPO |
| WO 93/21906 | 11/1993 | WIPO |
| WO 95/33434 | 12/1995 | WIPO |

OTHER PUBLICATIONS

Lee, K. et al., "Design of Oral Patches for the Treatment of Aphthous Stomatitis: Drug Layer", Yakche Hakhoechi 25(4):339–45 (S. Korea 1995); Chemical Abstracts 124(22), Abstract No. 298738 (May 27, 1996).

Allen, et al., "Mucus Glycoprotein Structure, Gel Formation and Gastrointestinal Mucus Function" in J. Nugent & M. O'Connor, Eds., Mucus and Mucosa, *Ciba Foundation Symposium 109*, Pitman, London, 137:137–156 (1984).

(List continued on next page.)

*Primary Examiner*—Peter F. Kulkosky
*Attorney, Agent, or Firm*—Arnall Golden & Gregory LLP

[57] ABSTRACT

Methods and compositions are provided for enhancing the bioadhesive properties of polymers used in drug delivery devices. The bioadhesive properties of a polymer are enhanced by incorporating a metal compound into the polymer to enhance the ability of the polymer to adhere to a tissue surface such as a mucosal membrane. Metal compounds which enhance the bioadhesive properties of a polymer include water-insoluble metal compounds such as water-insoluble metal oxides, including oxides of calcium, iron, copper and zinc. The metal compounds can be incorporated within a wide range of polymers including proteins, polysaccharides and synthetic biocompatible polymers. In one embodiment, metal oxides can be incorporated within polymers used to form or coat drug delivery devices, such as microspheres, which contain a drug or diagnostic agent. The metal oxides can be provided in the form of a fine dispersion of particles on the surface of a polymer that coats or forms the devices, which enhances the ability of the devices to bind to mucosal membranes. The polymers, for example in the form of microspheres, have improved ability to adhere to mucosal membranes, and thus can be used to deliver a drug or diagnostic agent via any of a range of mucosal membrane surfaces including those of the gastrointestinal, respiratory, excretory and reproductive tracts.

15 Claims, 1 Drawing Sheet